United States Patent [19]

Namba et al.

[11] Patent Number: 5,268,145
[45] Date of Patent: Dec. 7, 1993

[54] CHEMICAL SUBSTANCE-SENSING ELEMENT

[75] Inventors: Kenryo Namba, Tokyo; Yasuki Yoshida, Funabashi, both of Japan

[73] Assignee: TDK Corporation, Tokyo, Japan

[21] Appl. No.: 401,013

[22] Filed: Aug. 31, 1989

[30] Foreign Application Priority Data

| Sep. 1, 1988 | [JP] | Japan | 63-219439 |
| Sep. 2, 1988 | [JP] | Japan | 63-219921 |
| Oct. 18, 1988 | [JP] | Japan | 63-263506 |
| Aug. 18, 1989 | [JP] | Japan | 1-212791 |
| Aug. 18, 1989 | [JP] | Japan | 1-212792 |

[51] Int. Cl.$^5$ .................................. G01N 21/00
[52] U.S. Cl. ................................ 422/57; 436/73; 436/113; 436/169; 422/82.11
[58] Field of Search ............... 422/57, 58, 82.11, 56; 436/38, 73, 113, 169, 41

[56] References Cited

U.S. PATENT DOCUMENTS

| 2,460,071 | 1/1949 | Davis | 436/41 |
| 3,216,802 | 11/1965 | Smith | 436/41 |
| 3,350,175 | 10/1967 | McConnaughey et al. | 436/113 |
| 3,881,873 | 5/1975 | Klowden | 436/41 |
| 4,042,329 | 8/1977 | Hochstrasser | 436/169 |
| 4,129,417 | 12/1978 | White | 436/169 |
| 4,548,906 | 10/1985 | Sekikawa et al. | 436/113 |
| 4,649,123 | 3/1987 | Charlton et al. | 436/79 |

Primary Examiner—Lyle Alexander
Attorney, Agent, or Firm—Oblon, Spivak, McClelland, Maier & Neustadt

[57] ABSTRACT

A chemical substance-sensing element of the invention has a sensor film on a substrate, the sensor film containing a dye and a compound sensitive to a chemical substance such as water, for example, a hydrophilic compound. The sensor film contains a dye and a chemical substance sensitive compound in a common layer or is composed of a dye film and a film of a chemical substance sensitive compound laminated thereto. The light reflectance of the sensor film changes when the chemical substance sensitive compound bonds with a chemical substance to be detected. The chemical substance can be detected and quantitatively measured by directing light from a light-emitting element toward the sensor film and detecting the reflectance of the sensor film by means of a light-receiving element.

15 Claims, 6 Drawing Sheets

CHEMICAL SUBSTANCE-SENSING ELEMENT

BACKGROUND OF THE INVENTION

1. Field of the Invention

This invention relates to a chemical substance-sensing element forming a chemical substance sensor capable of detection and quantitative analysis of a chemical substance as well as a chemical substance-sensing device.

2. Prior Art

Chemical sensors are known which selectively adsorb or react with a particular chemical substance existing in an ambient environment and detects the type and concentration of the chemical substance from a change of electrical signal due to a change of resistivity or dielectric constant through such adsorption or reaction.

These chemical sensors are constructed from such materials as semiconductors, ceramics, and polymers and are in fact used for the detection and quantitative analysis of water vapor, various gases, various ions or the like.

Sensors using cholesteric liquid crystal are also known, see Japanese Patent Application Kokai Nos. 76094/1978 and 42685/1983, Tsukahara, Mechatronics, 6, 3 (1981), 103, Sensor Gijutsu (Sensor Technology), 7, 7 (1987), 62; ibid., 7, 11 (1987), 97; and ibid., 7, 12 (1987), 87.

These sensors utilize a color change of liquid crystal.

With the recent advance of office automation equipment, there is a need for sensors such as humidity sensors which can perform stably and precisely even in an environment having an increased electric field as found in copying machines. Sensors utilizing optical detection and quantitative analysis are advantageous for such purposes.

For such sensors, there is known an optical detection and quantitative analysis method which utilizes a change of optical absorption or fluorescence quantity (or extinction of fluorescence) of a certain dye or compound reacting with a gaseous substance or forming a charge transfer complex.

One known method utilizes a color change due to reaction of N,N-dimethylaniline with $O_2$ (see Japanese Patent Application Kokai No. 100337/1982).

Another known method utilizes a color change due to reaction of poly-2-para-(methacryloylaminophenyl)-5-phenyl-1,3-oxazole with $NH_3$ and amines (see Japanese Patent Application Kokai No. 202334/1985).

Also known is a method utilizing a fluorescence change due to reaction of tris(4,7-diphenyl-1,10-phenanthroline) Ru complex with $O_2$ (see Japanese Patent Application Kokai No. 178646/1986).

Additional known methods utilize an absorption change of a Thymol Blue film by $NH_3$ (see Nikkei Sangyo Shinbun, Dec. 14, 1987) and a fluorescence change of an LB film of a squalirium dye and a fatty acid by NOx (Japan Chemical Society, Spring Meeting Preprint, 3IIH07, 1988 and Nikkei Sangyo Shinbun, Jun. 10, 1988).

It has also been contemplated to apply metal or metal salt films in order to utilize optical reflection though such reports are a few.

For example, it is proposed to utilize reaction of palladium potassium sulfite with CO (see Japanese Patent Application Kokai No. 79141/1981), reaction of $HgBr_2$ with $AsH_3$ (see Japanese Patent Application Kokai No. 42645/1985), and corrosion of a metal film by $SF_4$ (see Japanese Patent Application Kokai No. 8066/1987).

Known humidity sensors utilize a change in refractive index of an optical fiber clad with a hygroscopic material (see Japanese Patent Application Kokai Nos. 217744/1986, 9255/1987, and 204143/1987);

a change in color of an inorganic material upon absorption of humidity (see Japanese Patent Application Kokai Nos. 80190/1979 and 139478/1981);

a change in coefficient of absorption or a change in scattering intensity or color development of a hygroscopic resin or the like (see Japanese Patent Application Kokai Nos. 67738/1981, 110039/1981, and 216936/1983);

a change of irregular reflection using a transparent member having an irregular surface and a hygroscopic agent (see Japanese Patent Application Kokai No. 204742/1984); and reflected light and transmitted light associated with a mirror consisting of two dielectric layers having different refractive indexes (see Japanese Patent Application Kokai No. 39744/1987).

Nevertheless, no proposal has been made as to the utilization of reflection of a dye film.

The above-mentioned sensors constructed from semiconductors, ceramics, and polymers have a drawback that the response is slow because of diffusion of a gas to be detected through a thick film. Many of them require regeneration. Often a change of resistance is detected by electric means which experiences a large change with time. In most cases, manufacture of such elements requires complicated steps and the detection circuit is complicated.

The sensors using cholesteric liquid crystal utilize a color change in proportion to a pitch change and have drawbacks including a widely varying or inconsistent wavelength distribution of light reflection, a low sensitivity, and considerable temperature dependency.

Utilization of a change of optical absorption or fluorescence quantity of a dye or the like has a drawback that the dye or the like must be able to selectively bond or react with a substance to be detected and quantitatively analyzed such as a gaseous substance. A highly advanced technique or a complicated step is necessary in manufacturing such an element. For example, in an element utilizing a change in fluorescence of an LB film, dye molecules must be oriented to high accuracy in applying the LB film. In an element utilizing a change in absorption of a Bromothymol Blue film, a reflective film must additionally be formed.

Further, sensors utilizing a metal or metal salt film have drawbacks that the reaction is irreversible in all cases, and the combination of a sensing material and a substance to be detected such as a gaseous substance is limited.

OBJECT OF THE INVENTION

An object of the present invention is to provide a chemical substance-sensing element which features a high precision and a quick response in detecting and quantitatively analyzing a chemical substance and which is of simple construction, durable and cost efficient.

SUMMARY OF THE INVENTION

Such an object is achieved by the present invention as defined below.

A chemical substance-sensing element in one form of the present invention includes a dye and a chemical substance sensitive compound wherein the light reflectance changes when the chemical substance sensitive compound bonds with a chemical substance to be detected.

A chemical substance-sensing device in another form of the present invention includes a chemical substance-sensing element having a substrate and a sensor film thereon, a light-emitting element, and a light-receiving element, wherein the sensor film contains a dye and a chemical substance sensitive compound wherein the light reflectance of the sensor film changes when the chemical substance sensitive compound bonds with a chemical substance to be detected, and the light-receiving element detects the change of reflectance of the sensor film, providing for detection and quantitative determination of the chemical substance.

BRIEF DESCRIPTION OF THE ACCOMPANYING DRAWINGS

FIGS. 1 and 2 are cross-sectional views of different embodiments of the chemical substance-sensing device according to the present invention.

FIGS. 3, 4, 5, 6, and 7 schematically illustrate further embodiments of the chemical substance-sensing device according to the present invention.

FIG. 8 is a perspective view showing a still further embodiment of the chemical substance-sensing device according to the present invention.

FIGS. 9, 10, and 11 are graphs showing the relationship of output voltage to relative humidity when the chemical substance-sensing device according to the present invention is used as a humidity sensor.

DESCRIPTION OF THE PREFERRED EMBODIMENTS

The construction of the present invention will be described in detail.

The chemical substance-sensing element of the present invention has a sensor film containing a dye and a chemical substance sensitive compound on a substrate.

In the practice of the invention, the sensor film may either contain a dye and a chemical substance sensitive compound in mixed, mutually dissolved or bonded form or be a laminate film consisting of a dye film containing a dye and a chemical substance sensitive film containing a chemical substance sensitive compound.

Figure 1:
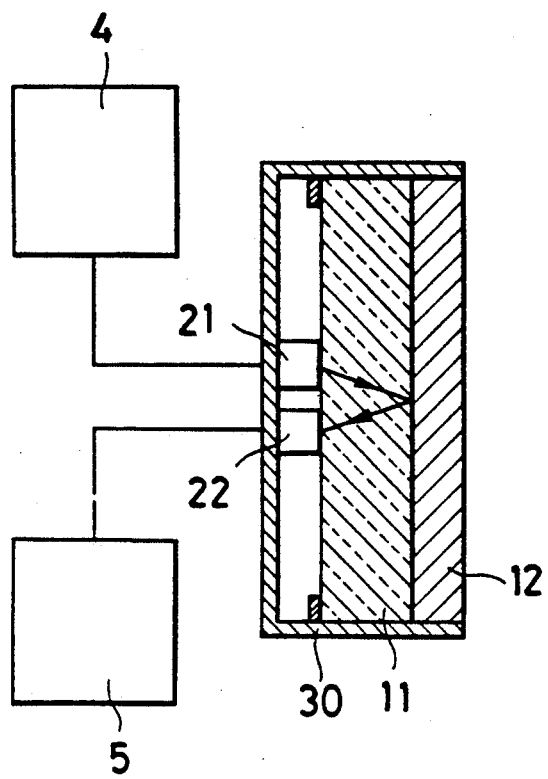

In the former case, as shown in FIG. 1, a sensor film 12 containing both a dye and a chemical substance sensitive compound is on a front surface of a substrate 11. Light emitting and receiving elements 21 and 22 are disposed on a rear surface of the substrate 11 remote from the sensor film 12. All the components are together housed in a casing 30.

Figure 2:
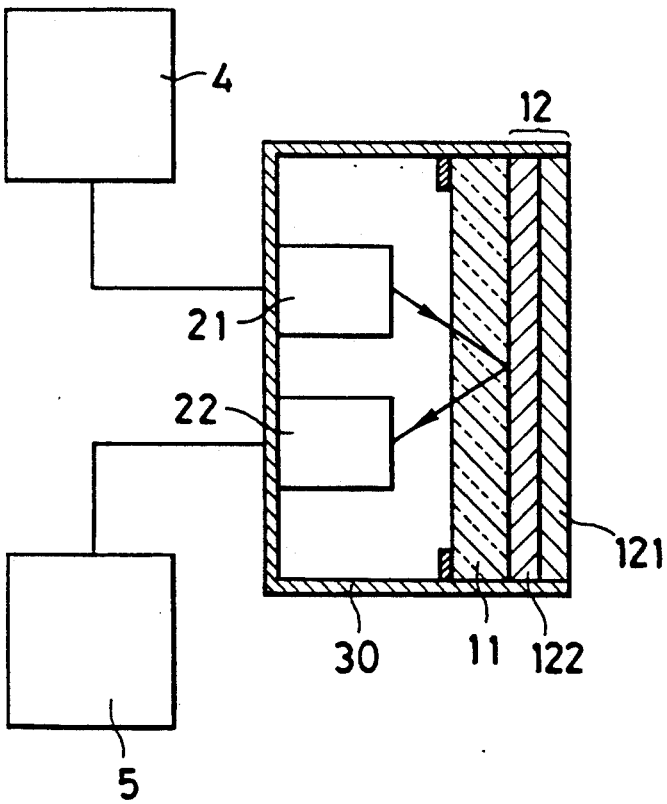

The construction for the latter case is the same as the chemical substance-sensing device of FIG. 1 except that the sensor film 12 is a laminate film consisting of a chemical substance sensitive film 121 containing a chemical substance sensitive compound and a dye film 122 containing a dye as shown in FIG. 2. In this form, the dye film 122 is preferably disposed adjacent the substrate 11 as shown in FIG. 2 because this arrangement enables detection from the rear surface of the substrate 11.

In the chemical substance-sensing devices shown in FIGS. 1 and 2, the light-emitting element 21 is connected to drive means 4 and the light-receiving element 22 is connected to detection means 5 for detecting and measuring the reflected light.

In these sensing devices, the light-emitting element 21 directs light toward the sensor film 12 from the rear surface of substrate 11 and the light-receiving element 22 captures the light specularly reflected by the sensor film 12 whereby a chemical substance to be detected is detected and quantitatively determined on the basis of a change of reflectance. Where the sensor film is a laminate film, the light reflected by the dye film is detected.

More particularly, in the chemical substance-sensing element shown in FIG. 1, the sensor film 12 containing a chemical substance sensitive compound changes its physical properties upon contact with a fluid under examination containing a chemical substance to be detected. For example, the chemical substance sensitive compound chemically bonds with a chemical substance to be detected to change the refractive index or thickness of the film.

Since the light reflection by the sensor film is due to multiple reflection within the film, such a change of physical properties of the film results in a change of reflectance.

Where the sensor film 12 is a laminate film as shown in FIG. 2, the multiple reflection within the dye film 122 is largely affected by the interface between the dye film and the chemical substance sensitive film. Therefore, when the chemical substance sensitive film changes its physical properties upon contact with a chemical substance to be detected, the reflectance of the dye film changes accordingly. Such interaction enables detection and quantitative determination of a chemical substance to be detected.

Where the sensor film is a laminate film, the film responsible for light reflection is the dye film which exhibits a high reflectance due to multiple reflection. It is, however, undesirable to use a metal film instead of the dye film because the metal film has a high reflectance at its surface and offers little multiple reflection effect.

The sensor film in the form of a laminate film eliminates any consideration about the compatibility between the chemical substance sensitive compound and the dye which must be carefully chosen for a single film containing both the chemical substance sensitive compound and the dye. Therefore the content of dye in the dye film can be maximized to provide for a sufficient change of reflectance, leading to increased sensitivity. Since the chemical substance sensitive compound can be selected from a wide range without considering its compatibility with the dye, the range of chemical substance to be detected is accordingly increased. A desired sensitivity can be obtained by controlling the thickness of the dye film.

In the practice of the invention, the light emitting and receiving elements 21 and 22 are preferably disposed in close proximity because sensitivity is increased by measuring the light given by specular reflection at an incident angle of 20 degrees or less and because the element becomes compact as a whole. The compactness and integrity of the element is increased by integrally attaching the light emitting and receiving elements 21 and 22 to the rear surface of the substrate 11.

The dye used herein is not critical although preferred are dyes exhibiting specular reflection for at least one wavelength within the spectrum of light emitted by the light-emitting element 21, more illustratively, a reflectance of at least 10%, more preferably at least 20% at an incident angle of up to 20°, especially about 5°. The dyes of such nature are known as bronzing dyes. With a reflectance of less than 10%, it would become difficult to detect the chemical substance under analysis by way of a reflectance change.

In the practice of the invention, the light emitted by the light-emitting element has a wavelength in the spectrum of from visible to infrared. The dye used herein, in a dye film form, may have an absorbance of up to 70%, preferably up to 50% at the wavelength used. It is desired that the maximum reflection wavelength ($\lambda$Rmax) of the dye film is different from the maximum absorption wavelength ($\lambda$Amax), especially $\lambda$Rmax$-\lambda$Amax$\geq$50 nm. The use of these dyes ensures a substantially satisfactory sensitivity.

The dyes are not particularly limited as long as they have a reflectance of at least 10% at the above-mentioned wavelength. Illustrative examples thereof include cyanine dyes, azulenium dyes, pyrylium dyes, squarilium dyes, chloconium dyes, quinone-naphthoquinone dyes, metal complex dyes, phthalocyanine dyes, naphthalocyanine dyes, and the like.

Where polymethine dyes as typified by cyanine dyes are used, a singlet oxygen quencher may be used. Preferred quenchers include metal complexes, especially Ni complexes, for example, nickel complexes of dithiol series (especially bisphenyldithiol series) and amine compounds.

In the practice of the invention, the chemical substance sensitive compound contained in the sensor film or the chemical substance sensitive film should bond with a particular chemical substance in a reversible or irreversible manner and may be selected in accordance with a chemical substance under analysis.

More particularly, the chemical substance sensitive compound can form various molecular bonding states with a chemical substance to be detected, the bonding states encompassing various reactions and various bonds including a covalent bond, ionic bond, and coordinate bond, as well as adsorption and absorption.

The bond and release of the chemical substance sensitive compound to and from the chemical substance under analysis is preferably reversible, thought it may be irreversible.

When the invention is applied to a humidity sensor, that is, the chemical substance under analysis is water, a hydrophilic compound is used as the chemical substance sensitive compound.

The hydrophilic compounds used herein desirably have a solubility parameter (SP) $\delta=$(CED)$^{\frac{1}{2}}$ of at least 17 (MJ/m$^3$)$^{\frac{1}{2}}$, especially 17 to 40 (MJ/m$^3$)$^{\frac{1}{2}}$, more preferably 18 to 40 (MJ/m$^3$)$^{\frac{1}{2}}$, most preferably 20 to 30 (MJ/m$^3$)$^{\frac{1}{2}}$ wherein CED is a cohesive energy density.

The solubility parameter is calculated by the following methods or determined from actual measurements.

A: Calculation from Heat of Evaporation

Calculation may be made from the equation:

$$\delta = (Ev/v)^{\frac{1}{2}}$$

wherein Ev is a molar evaporation energy (J/mol), and v is a molar volume (m$^3$/mol).

Since a high-molecular weight compound does not evaporate, its solubility parameter is calculated by method B or C.

B: Actual Measurement from Compatibility (1) Swell

Since a cross-linked three-dimensional high-molecular weight compound is insoluble in a solvent, the swell of the compound in various solvents is examined. The SP value of the solvent achieving the maximum swell is regarded as the SP value of the high-molecular weight compound (see D. Mangaraj, Macromol. Chem., 65, 29 (1963)).

(2) Viscosity

A high-molecular weight compound shows an increased viscosity in a well compatible solvent because the high molecular chain is widespread therein. The compound is measured for intrinsic viscosity $\eta$ in various solvents. The measured intrinsic viscosities are plotted relative to the SP values of the solvents used. An SP value corresponding to a maximum is regarded as the SP value of the high-molecular weight compound (see D. Mangaraj, S. Patra and S. B. Rath, Macromol. Chem., 67, 84 (1963), ibid, 65, 39 (1963) and G. M. Bistow and W. F. Watson, Trans. Faraday Soc., 54, 1742 (1958)).

(3) Turbidity

To a solution of a high-molecular weight compound is added dropwise a poor solvent for the compound. The SP value of the high-molecular weight compound is determined from the amount of the poor solvent added until the solution becomes turbid and the SP value of the poor solvent (see K. W. Suh and D. H. Clarke, J. Polym. Sci., 5, 1671 (1967) and K. W. Suh and J. M. Corbett, J. Appl. Polym. Sci., 12, 2359 (1968)).

C: Calculation from Chemical Structure

Calculation may be made according to Small's method (P. Small, J. Appl. Chem., 3, 71 (1953)), more preferably Fedors' method (R. F. Fedors, Polym. Eng. Sci., 14, 147 (1974)), using the evaporation energy $\Delta$ei and the molar volume $\Delta$vi of an atom and a grouping.

In the practice of the invention, at least one of the hydrophilic compounds used may have an SP value of at least 17 (MJ/m$^3$)$^{\frac{1}{2}}$ as calculated by Method A, B or C mentioned above.

Also, at least one of the hydrophilic compounds used may preferably have a contact angle with water of up to 70°, more preferably from 10° to 70° when formed as a monolayer film.

Several illustrative examples of the hydrophilic compounds belonging to the chemical substance sensitive compounds are given below.

I. HYDROPHILIC HIGH-MOLECULAR WEIGHT COMPOUNDS

Hydrophilic high-molecular weight compounds should preferably have a polar group, that is, a polar atom or grouping in order that they have a desirable SP value or contact angle with water.

The polar group-containing high-molecular weight compounds include oxygen-containing high-molecular weight compounds such as having a carbonyl or ether group and NH group-containing high-molecular weight compounds as well as high-molecular weight compounds having a cyan group, halogen, acid residue or the like. More illustrative examples are given, below.

a) Hygroscopic High-Molecular Weight Anion Salts (Especially Salts Capable of Reversible Water Absorption)

For example, sodium alginate, sodium polyacrylate, sodium polymethacrylate, sodium poly(4-styrenesulfonate), sodium polyvinyl phosphate, ammonium polyvinyl phosphate, sodium polyglutamate, etc.

b) High-Molecular Weight Electrolytes

For example, polyethyleneimine hydrochloride, polyethyleneimine/polystyrene sulfonate, and poly-N-methylchloropyridinium, etc.

c) Thermosetting Resins

Phenol resins, furan resins, alkyd resins, epoxy resins, melamine resins, unsaturated polyester resins, etc.

d) Thermoplastic Resins

Polyvinyl acetate, polyacrylate, polymethacrylate, polyvinyl chloride, polyacrylonitrile, polyvinyl alcohol, polyethers, polyamides, polyesters, polyurethanes, polyvinyl ketone, polyvinylidene chloride, polyvinyl pyrrolidone (PVP), polyalkylene glycols (e.g., polyethylene glycol), polyacrylamides, PVA-ethylene copolymers, etc.

e) Celluloses

Acetylcellulose, triacetylcellulose, nitrocellulose, acetylbutylcellulose, propionylcellulose, ethyl cellulose, carboxymethyl cellulose, etc.

f) Natural High-Molecular Weight Compounds and Their Derivatives

Casein, amylose, polyglycine, and modified starch (grafted starch), etc.

g) Blends or Copolymers of the Foregoing Compounds

It is to be noted that these compounds may have a three-dimensional structure resulting from crosslinking.

These high-molecular weight compounds are advantageously used because of good film properties and high water resistance.

II. HYDROPHILIC LOW-MOLECULAR WEIGHT ORGANIC COMPOUNDS h) Hygroscopic Organic Metal Salts (Especially Salts Capable of Reversible Water Absorption)

For example, sodium acetate, sodium potassium tartrate, sodium lactate, etc.

III. HYDROPHILIC INORGANIC COMPOUNDS i) Hygroscopic Inorganic Metal Salts (Especially Salts Capable of Reversible Water Absorption)

Metal halides such as $LiCl_2$, $CaCl_2$, $CoCl_2$, etc.

j) Hydrophilic Gels

For example, colloidal silica and hydrolyzates of silicates, titanates, aluminates, zirconates, etc., such as silicon alkoxide.

These compounds may be used alone or in admixture of two or more. The use of these compounds provides a humidity sensor for detecting water vapor.

Where ammonia is a chemical substance to be detected, use may be made of Bromothymol Blue, Thymol Blue, Acridine Orange, poly-2-para-(methacryloylaminophenyl)-5-phenyl-1,3-oxazole, and the like.

Where the chemical substance to be detected is an alkali metal or alkaline earth metal ion such as $Na^+$ and $K^+$ or another metal ion such as $Ag^+$, a crown ether is useful.

Examples of the crown ether which can be used herein include benzo-15-crown-5 (chemical substance on analysis: $Na^+$), dibenzopyridino-18-crown-6 (chemical substance on analysis: various metal ions), kryptofix 222 CC (manufactured by Merck) (chemical substance on analysis: $K^+$), azacrown ether having a long chain introduced therein (chemical substance on analysis: $Ag^+$), for example,

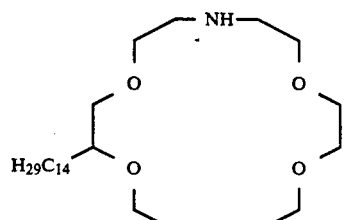

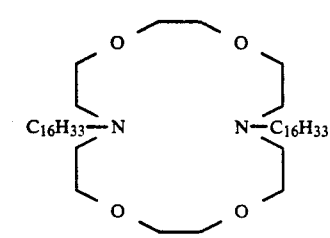

and the like.

Other useful sensitive compounds are cholesteric liquid crystal for various gases, pyrene, N,N-dimethylaniline, and tris(4,7-diphenyl-1,10-phenanthroline) Ru complex for $O_2$ as the chemical substance on analysis, and triphenylmethine Neutral Red for $(ClCH_2CH_2)_2S$ or $(ClCH_2CH_2)_2NH$ as the chemical substance on analysis.

It is presumed that a film containing a chemical substance sensitive compound as described above changes its physical properties in the following manner.

The hydrophilic compound, for example, changes film properties upon hydration with water vapor or adsorption or absorption of water.

Bromothymol Blue or the like is presumed to change film properties through any interaction with ammonia eventually resulting in formation of a charge transfer complex.

The crown ether is presumed to change film properties through inclusion of an alkali metal or alkaline earth metal ion.

Bonding between the chemical substance sensitive compound and a chemical substance on analysis may be either reversible or irreversible bonding which can change the optical reflectance of the film. Reversible bond is preferred from the standpoint of possible repetitive use of the sensor.

In the practice of the invention, only a change in light reflectance may be utilized as described above although a change in light transmittance may be utilized in combination therewith, if desired.

In addition to a change in light reflectance for monochromatic light, a certain spectrum of wavelength may be used for measurement to detect a change in quantity of reflected light. In such a case, an LED may desirably be employed as the light source, resulting in an increased change in light quantity.

In these cases, specular reflection is preferably utilized as previously described.

In the sensor film of the chemical substance sensor of the configuration shown in FIG. 1, the dye and the chemical substance sensitive compound may be used in mutually dissolved form or in admixture. Also, part of the chemical substance sensitive compound may bond with the dye.

It is preferred for sensor performance that the sensor film consists of the dye and the chemical substance sensitive compound although the film may further contain nitrocellulose or a resin such as polystyrene and nylon as a binder. The chemical substance sensitive compound may be blended with the dye in a proportion of 0.01 to 40% by weight, preferably 0.1 to 10% based on the weight of the dye. Within this proportion, bonding of the chemical substance sensitive compound with a chemical substance on analysis is reflected as a sufficient change of film property.

The sensor film is preferably a thin film because a thin film can provide a quick response as a sensor. The thickness of the sensor film preferably ranges from 400 to 2,000 Å, more preferably from 500 to 1,000 Å.

When the sensor film is a laminate film as shown in FIG. 2, the chemical substance sensitive film may preferably consist of a chemical substance sensitive compound if it can be formed into a film without aids.

More particularly, for the manufacture of humidity sensors, the hydrophilic high-molecular weight compounds among the above-enumerated examples can form a coating having good film properties. Sensitivity can be improved by adding a hygroscopic inorganic metal salt thereto. Poly-2-para-(methacryloylaminophenyl)-5-phenyl-1,3 oxazole or the like may be similarly processed where ammonia is a chemical substance to be detected. It is to be noted that other compounds may be formed into a film by coating or evaporation.

It is also possible to form a sensor film using a combination of chemical substance sensitive compounds which are sensitive to the same chemical substance. In this case, a chemical substance sensitive compound with a high-molecular weight may additionally possess a binder function.

It is permissible to use binders such as various polymers along with the chemical substance sensitive compounds as long as the binders do not obstruct the function of the chemical substance sensitive compounds.

The content of the chemical substance sensitive compound in the chemical substance sensitive film preferably ranges from 50 to 100% by weight, more preferably from 80 to 100% by weight. Within this content, the sensor film provides a sufficient change of film property.

The chemical substance sensitive film is preferably a thin film because a thin film can provide a quick response. The thickness of the chemical substance sensitive film preferably ranges from 0.05 to 100 μm, more preferably from 0.1 to 5 μm.

The dye film may consist of a dye or further contain a binder, for example, a self-oxidizing resin such as nitro-cellulose, and a thermoplastic resin such as polystyrene and nylon. The content of the dye in the dye film preferably ranges from 60 to 100% by weight, more preferably from 90 to 100% by weight. Within this content, a change of film property can be reflected as a sufficient change of light reflectance.

The dye film generally has a thickness of from about 400 to about 2,000 Å although the exact thickness may be selected depending on the desired sensitivity and other factors.

The substrate 11 used in the practice of the invention is not particularly limited with respect to its material. Preferably it is substantially transparent to the light emitted by the light-emitting element 21 because transparency allows for detection from the side of substrate 11 as shown in the figures.

Illustrative examples of the substrate include glass and various resins such as rigid vinyl chloride, polyethylene terephthalate (PET), polyolefins, polymethylmethacrylate (PMMA), acrylic resins, epoxy resins, poly-carbonate resins, polysulfone resins, polyether sulfones, methylpentene polymers, bisphenol-A-terephthalate copolymers, etc.

The substrate 11 used in the practice of the invention is generally in the form of a plate or film which may be dimensioned in accordance with the light emitting and receiving elements. The sensor film is formed on at least one surface, usually one major surface of the substrate. Increased mass productivity is expected by forming a sensor film on a substrate and punching or cutting to desired dimensions.

The side surfaces of the substrate 11 except the light incident surface may be provided with a reflective layer. The reflective layer may be formed from aluminum, gold or the like. Provision of the reflective layer results in increased detection sensitivity.

The light-emitting element 21 used in the practice of the invention is not critical although a light emitting diode (LED), laser diode (LD) and similar elements are preferred. Also, the light-receiving element 22 is not critical although a photo diode, photo transistor and similar elements are preferred.

The light emitted by the light-emitting element 21 may be delivered to the sensor film in a continuous manner, but preferably in an intermittent manner. Intermittent exposure can minimize the temperature rise of the sensor film. Then, bonding of the chemical substance sensitive compound in the sensor film with a chemical substance to be detected is little affected by heat, resulting in a significantly improved measurement precision upon continuous measurement.

The exposure time for intermittent exposure is not critical. Preferably, the exposure time is as short as possible insofar as reflectance can be measured, for example, from about 0.01 to about 100 msec. Also, the exposure interval is not critical. Preferably, the exposure interval is as long as possible insofar as a necessary measurement interval is met, in order to avoid a significant temperature rise of the sensor film. For example, the exposure interval is about 0.1 to about 10 msec. for ordinary humidity sensors.

In the practice of the invention, the drive means 4 and the detecting means 5 are preferably disposed apart from the sensor film 12. This configuration helps prevent a temperature rise of the sensor film 12. The spacing of the drive means and the detecting means from the sensor film varies with the amount of heat generated by these means, but is preferably at least about 0.1 mm. The exact spacing may be determined through experimentation.

In the embodiments shown in FIGS. 1 and 2, the light-receiving element 22 for detecting a change of reflectance is disposed in proximity to the light-emitting element 21 on the rear surface of the substrate. This configuration affords the above-mentioned advantages although the invention is not necessarily limited to these embodiments.

Figure 3:
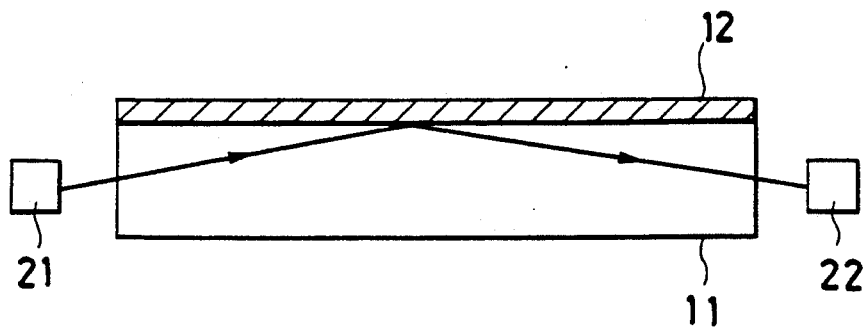

Another useful embodiment is shown in FIG. 3, for example. More particularly, the light emitting and receiving elements 21 and 22 are disposed such that the light from the light-emitting element 21 is angularly incident on one side surface of the four side surfaces of the substrate 11 and the light-receiving element 22 picks up the light reflectance. The three side surfaces of the substrate 11 excluding the light incident surface may be provided with a reflective layer.

Figure 4:
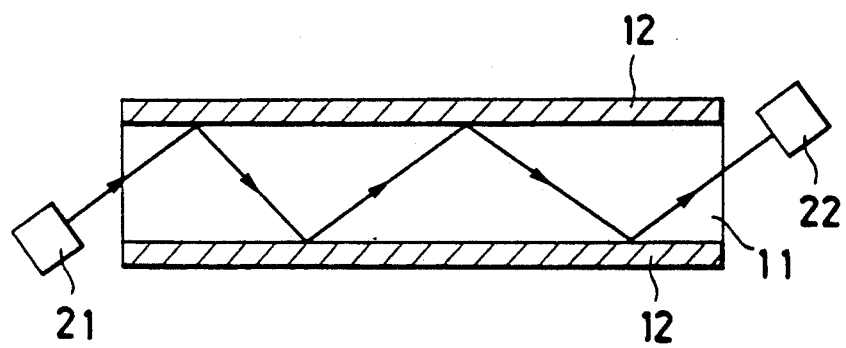

The embodiment of FIG. 3 is designed to effect detection after single reflection. Detection sensitivity can be improved with the embodiment of FIG. 4 wherein sensor films 12 are formed on the opposite surfaces of a substrate 11 to ensure multiple reflection. The number of light turns may be 2 to 8, preferably 3 to 5.

Figure 5:
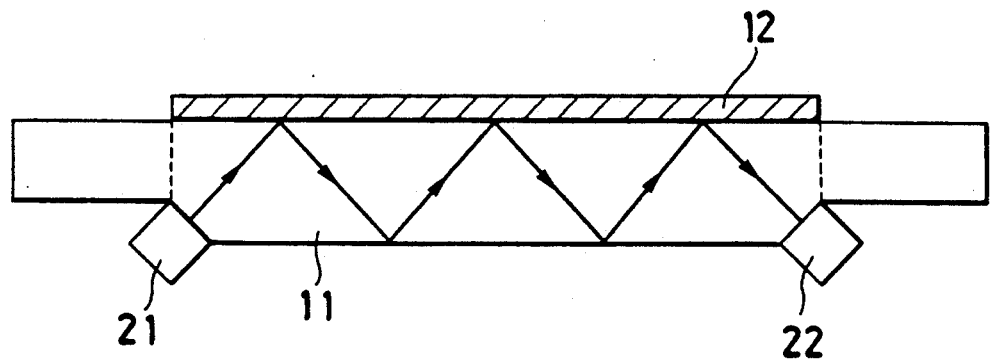

A still further embodiment is shown in FIG. 5 wherein the substrate 11 on the rear surface is provided with bevel sections having angles corresponding to the incident angle and exit angle, and the light emitting and receiving elements 21 and 22 are attached to the bevel sections for integration to the substrate 11. This configuration results in an element with improved compactness and integrity. Sensor films 12 may be formed on the opposite surfaces of the substrate in this embodiment too.

Figure 6:
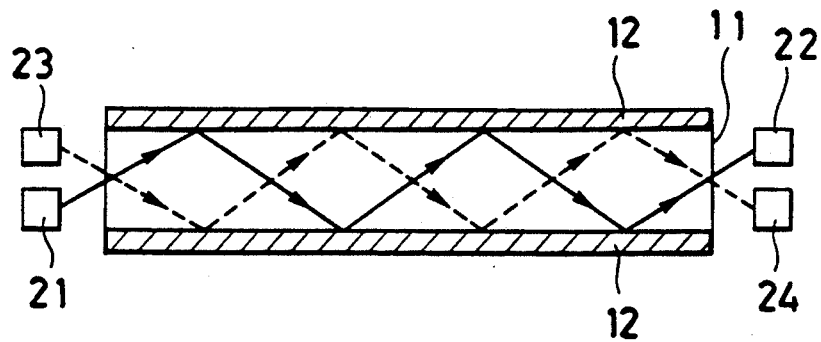

A yet further embodiment is shown in FIG. 6 wherein sensor films 12 are formed on the opposite surfaces of the substrate 11, light-emitting elements 21 and 23 emit light at different wavelengths, and light-receiving elements 22 and 24 detect the reflectance of the respective wavelengths. This arrangement results in an increased detection precision.

In this embodiment, one of the films on the opposite surfaces of the substrate 11 can be a reference film free of a chemical substance sensitive compound to improve detection precision.

The respective sensor films 12 may be films of different chemical substance sensitive compounds which can independently detect two chemical substances such that for a mixture of two chemical substances to be detected, the proportion of the respective chemical substances can be identified.

Figure 7:
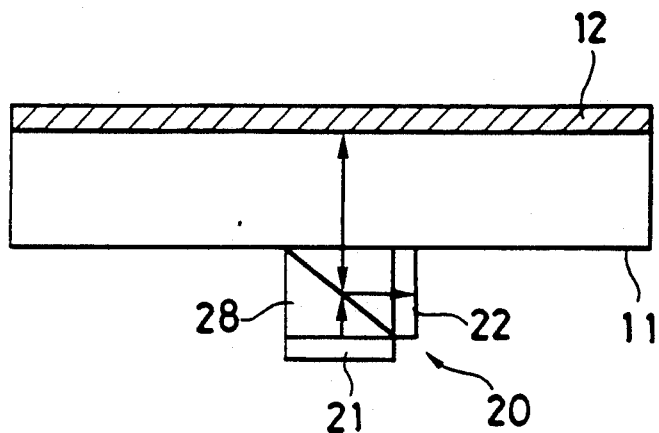

A further arrangement for detecting reflected light is shown in FIG. 7 wherein a light emitting/receiving section 20 in which a half mirror in the form of a prism 28 is incorporated with the light emitting and receiving elements 21 and 22 is attached to the rear surface of the substrate 11 remote from the surface where the sensor film 12 is formed. Incorporation of elements contributes to the compactness and integrity of the sensor. In the practice of the invention, it is preferred to incorporate light emitting and receiving elements together into a single element like this embodiment because the device becomes more compact.

Figure 8:
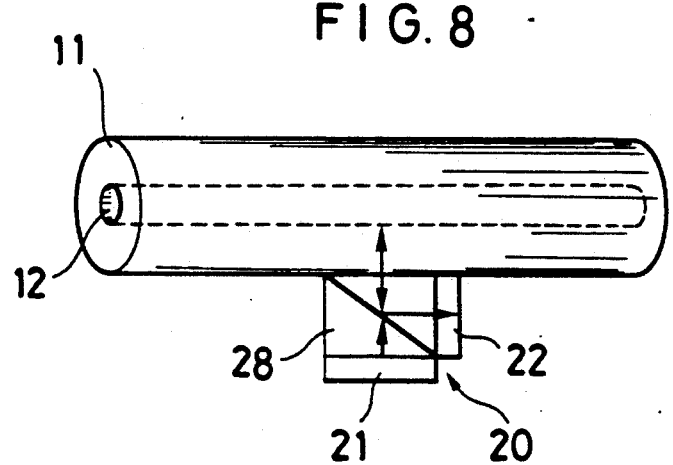

Further, the substrate 11 may be a cylinder or bar rather than a plate or film. For example, FIG. 8 shows a substrate 11 in the form of a hollow cylinder having a sensor film 12 formed on the inner bore surface.

In this embodiment, a fluid containing a chemical substance to be detected is passed through the bore. A light emitting/receiving section 20 in which a prism 28 is combined with the light emitting and receiving elements 21 and 22 is attached to the outer periphery of the substrate 11 as in the preceding embodiment. The dimensions of the sensing element used in the embodiment are not critical although the cylinder preferably has an outer diameter of about 1 to 10 mm, a length of about 3 to 20 mm, and a bore diameter of about 0.5 to 8 mm.

Besides the illustrated embodiments, the substrate may be a glass fiber which is provided at an end surface with a sensor film. Also useful is a bundle of a plurality of such glass fibers. It is also useful to bind glass fibers into a bundle with a resin or the like, polish an end surface of the fiber bundle, and form a sensor film thereon. In these embodiments, light emitting and receiving elements are located on another end surface remote from the sensor film bearing surface.

Any other variations may occur on the arrangement using the sensor film according to the invention.

In the practice of the invention, a gas-permeable protective plate may be provided on the surface of the sensor film to be in contact with the fluid on analysis. For such a purpose, the gas-permeable protective plate may be disposed to construct an air sandwich structure or in close contact with the sensor film. Also, a filter which allows passage of a particular chemical substance may be provided on the surface of the sensor film.

In all these embodiments, the light emitting and receiving elements are preferably located and integrated such that they avoid contact with the fluid on analysis. More particularly, only the sensor film is exposed to the fluid on analysis whereas the light emitting and receiving elements may be received in a casing or molding together with the substrate.

In the chemical substance sensing element of the invention, the sensor film is fabricated by preparing a coating solution or solutions containing a dye and a chemical substance sensitive compound in accordance with a particular sensor film construction and forming a coating or coatings on a substrate. Such coatings may be formed by spin coating, dipping, spraying or the like.

The solvents are not critical insofar as the dye and the chemical substance sensitive compound used are soluble in them. Examples include keto-alcohols (aliphatic keto-alcohols, especially diacetone alcohol, acetol, acetoin, acetoethyl alcohol, etc.), ethers represented by $R^1O$—$R^2$—$OH$ wherein $R^1$ is a lower alkyl group (especially having 1 to 5 carbon atoms) and $R^2$ is a lower alkylene group (especially having 2 to 5 carbon atoms), ketones such as methyl ethyl ketone, methyl isobutyl ketone, cyclohexanone, etc., esters such as butyl acetate, ethyl acetate, carbitol acetate, butylcarbitol acetate, etc., ethers such as methyl cellosolve, ethyl cellosolve, etc., aromatics such as toluene, xylene, etc., haloalkyls such as dichloroethane, etc., water, alcohols and the like.

Where the sensor film is a monolayer structure as shown in FIG. 1, a sensor film containing a dye and a metal halide may be prepared as follows.

When the dye is in the form of a soluble salt having an anion radical ($-SO_3$—radical, $-COO$—radical, $-PO_4^{2-}$—radical) and a positive counter ion paired with the anion radical such as Na, K, and $NH_4$, the sensor film may be prepared by forming a coating of the dye as previously described and subjecting the positive counter ion to salt exchange while simultaneously introducing a metal halide into the film.

This method is advantageous when the salt form of the desired dye is difficultly soluble in a coating solvent, and particularly when the chemical substance sensitive compound is a metal halide or the like. Then the metal halide such as $CaCl_2$ should be present in the coating in such form. To this end, the coating after immersion in a salt exchange solution is ready for use simply after drying or by washing with water or wash liquid and immersing again in another salt solution of a similar composition to the salt exchange solution. The salt exchange preferably takes place partially. The salt exchange solution of $CaCl_2$ or the like may have a concentration of 1 to 10% by weight, preferably 2 to 5% by weight.

The solvent for the salt exchange solution may be selected from the same types as described for the coating solvent. However, it is necessary that the dye resulting from salt exchange and the substrate are substantially insoluble in the solvent whereas a salt of the counter ion resulting from salt exchange is soluble in the solvent.

The salt exchange may proceed at a temperature of 0 to 60° C. for about 1 to about 60 minutes. The film thickness used herein may range from about 0.05 to about 0.1 μm and be suitably chosen in accordance with the amount of $CaCl_2$ or the like introduced.

The dyes used in this method may be polymethine dyes, for example, cyanine dyes, azulenium dyes, pyrylium dyes, and thiapyrilium dyes, with the dyes forming salts. Preferred among the polymethine dyes are cyanine dyes, especially cyanine dyes having an indolenine ring. For detail of the preferred dyes, reference is made to Japanese Patent Application Kokai Nos. 194595/1983, 202892/1984, 55794/1984, 55795/1984, 81194/1984, and 83695/1984.

It is to noted that the difficultly soluble salt resulting from salt exchange is quite stable to a chemical substance to be detected, such as water.

In the case of a laminate sensor film as shown in FIG. 2, a chemical substance sensitive film may be prepared as follows when the chemical substance sensitive compound used is a hygroscopic high-molecular weight anion salt.

When the chemical substance sensitive compound is in the form of a soluble salt having an anion radical and a positive counter ion paired with the anion radical such as Na and $NH_4$, the sensitive film may be prepared by forming a coating of the chemical substance sensitive compound as previously described and subjecting the positive counter ion to salt exchange while simultaneously introducing a metal halide into the film.

By converting the soluble salt into an insoluble form through salt exchange, the coating is improved in stability, for example, it becomes fully stable to a chemical substance to be detected, such as water. The function of the chemical substance sensitive film can be improved by leaving excess metal halide such as $CaCl_2$ in the coating. Then the metal halide such as $CaCl_2$ should be present in the coating in such form. To this end, the coating after immersion in a salt exchange solution is ready for use simply after drying or by washing with water or wash liquid and immersing again in another salt solution of a similar composition to the salt exchange solution.

The salt exchange solution of $CaCl_2$ or the like may have a concentration of 1 to 10% by weight, preferably 2 to 5% by weight.

The solvent for the salt exchange solution may be selected from the same types as described for the coating solvent. However, it is necessary that the high-molecular weight anion salt resulting from salt exchange and the substrate are substantially insoluble in the solvent whereas a salt of the counter ion resulting from salt exchange is soluble in the solvent.

The salt exchange may proceed at a temperature of 0 to 60° C. for about 1 to about 60 minutes. The film thickness used herein may range from about 0.05 to about 0.1 μm and be suitably chosen in accordance with the amount of $CaCl_2$ or the like introduced.

In this embodiment of the invention, the sensor film may be formed by evaporation. That is, the sensor film may be formed by a well-known method using the dye and/or chemical substance sensitive compound as the evaporation source. The dyes used herein include phthalocyanine dyes, naphthalocyanine dyes, squarilium dyes, croconium dyes, and the like.

The light emitting and receiving element according to the present invention may be installed by any well-known method.

The chemical substance sensor of the present invention allows the sensor film or chemical substance sensitive film to be controlled in thickness and can detect a chemical substance in a concentration ranging from ppb to 100%, depending on a particular film thickness, by contacting the film with a fluid containing the chemical substance to be detected.

BENEFITS OF THE INVENTION

The chemical substance sensor of the present invention is adapted for detection and quantitative determination of a chemical substance in a fluid on analysis.

The invention enables measurement from the rear surface of a substrate because the dye is used for measurement of a light reflectance. No limit is imposed on the choice of the dye because the chemical substance to be detected selectively bonds with the chemical substance sensitive compound.

Possible formation of a thin film provides a quick response. The chemical substance is measurable over a wide range of concentration with improved linearity.

The sensor construction is simple, ensuring compactness and ease of manufacture.

The sensor is cost efficient because it eliminates such manufacturing steps as sintering and molding as well as electrodes or the like.

Devoid of electrical interaction such as transfer of electrons and application of voltage to the chemical substance sensitive film, the sensor experiences minimized degradation and withstands continuous operation.

The sensor is durable in that signal detecting elements such as light emitting and receiving elements can be kept off from the chemical substance to be detected.

EXAMPLE

Examples of the invention are given below by way of illustration.

EXAMPLE 1

A sensing device of the configuration shown in FIG. 1 was constructed.

The sensor film was prepared as follows.

A methanol solution of

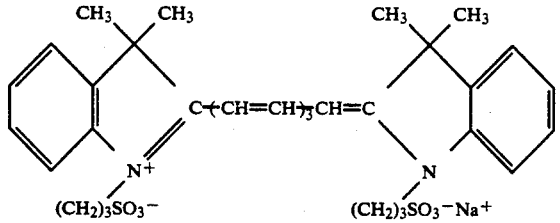

was coated on a PET film (0.1 mm thick) as a substrate, forming a thin film of about 700 Å thick. The thin film was immersed in an aqueous solution of 3% by weight of $CaCl_2$ for one minute for salt exchange. The substrate was taken out of the solution and dried on a spinner. It was further dried in a dryer (70° C., 1 hour).

There was formed a film containing the Ca salt of said dye and CaCl$_2$. It is to be noted that a monolayer film of CaCl$_2$ had a contact angle with water of up to 70°.

Then a disk having a diameter of 7 mm was punched out of the coated substrate.

The light emitting element in the form of an LED emitting light at a wavelength of 950 nm and the light receiving element in the form of a PIN diode were integrally attached to the rear surface of the disk. The assembly was received in a casing such that the sensor film was exposed.

Figure 9:
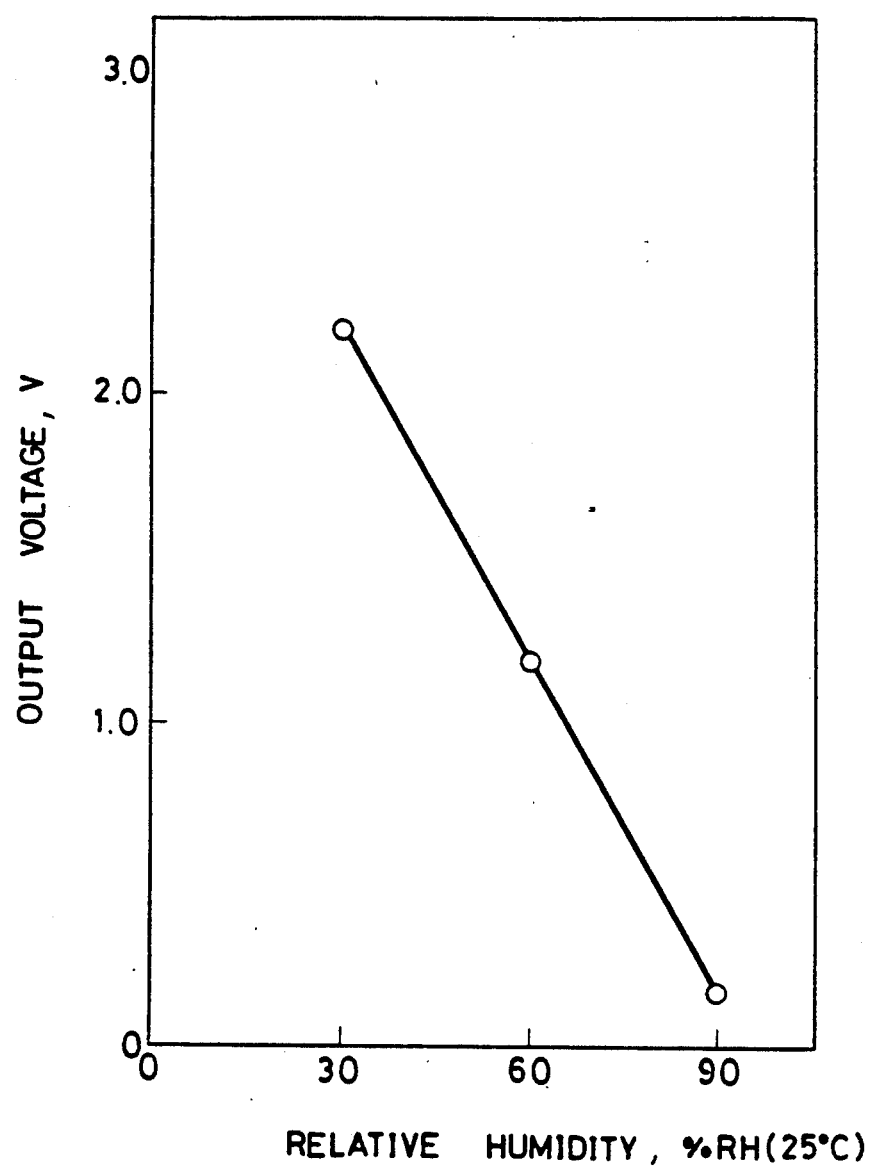

On use in humidity measurement, the sensing device could measure water vapor over a concentration range of 30 to 90% RH. FIG. 9 shows the relationship of the output voltage of the sensing device to relative humidity.

The results show that the concentration was measurable over a wide range with improved linearity.

Next, continuous measurement was carried out for 10 minutes in an atmosphere of 33% RH by driving the light emitting element with an operating time of 0.1 msec. and an operating interval of 0.9 msec.

The intermittent exposure resulted in a reduced change of output voltage as compared with continuous exposure.

EXAMPLE 2

A sensing device was constructed by the same procedure as in Example 1 except that the following chemical substance sensitive film was used.

Preparation of Chemical Substance Sensitive Film

A methanol solution containing

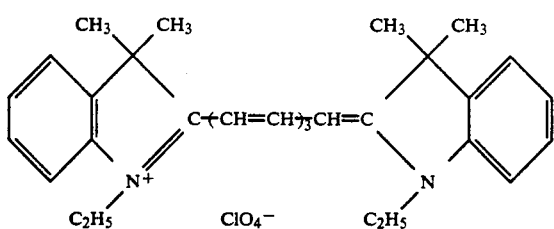

and CaCl$_2$ in a weight ratio of 1:0.05 was coated on a PET film, forming a thin film of 800 Å thick.

This sensing device showed equivalent results to Example 1.

EXAMPLE 3

A sensing device was constructed by the same procedure as in Example 1 except that the sensor film was prepared as follows.

Preparation of Sensor Film

A methanol solution containing

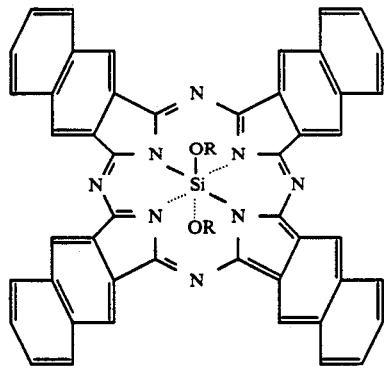

(R:Si(CH$_3$)$_2$O$-$(C$_2$H$_4$O)$_{3}$C$_4$H$_9$)

and LiCl$_2$ in a weight ratio of 1:0.1 was coated on a PET film in the same manner as in Example 1, forming a thin film of 700 Å thick. It is to be noted that a monolayer film of LiCl$_2$ had a contact angle with water of up to 70°.

On use in humidity measurement, the sensing device could measure water vapor over a concentration range of 30 to 90% RH.

EXAMPLE 4

A sensing device of the configuration shown in FIG. 1 was constructed by the same procedure as in Example 1.

The sensor film was prepared as follows.

The dye used in Example 2 and Bromothymol Blue were mixed in a weight ratio of 1:0.03, and the mixture was coated on a PET film in the same manner as in Example 1, forming a thin film of 800 Å thick.

Air containing ammonia gas was passed along the sensing device, which showed a reduction of reflectance.

EXAMPLE 5

A sensing device was constructed by the same procedure as in Example 1 except that the sensor film was prepared by coating a water-methanol solution containing the dye (Na salt) of Example 1 and polyvinyl pyrrolidone (which in a monolayer film had an SP value of at least 20 (MJ/m$^3$)$^{\frac{1}{2}}$ and a contact angle of up to 70°) in a weight ratio of 0.9:0.1.

This sensing device showed equivalent results to Example 1.

EXAMPLE 6

A sensing device was constructed by the same procedure as in Example 5 except that the polyvinyl pyrrolidone was replaced by PVA (which in a monolayer film had an SP value of 26 (MJ/m$^3$)$^{\frac{1}{2}}$ and a contact angle of up to 70°).

This sensing device showed equivalent results to Example 1.

EXAMPLE 7

A methanol solution containing 2% by weight of a dye:

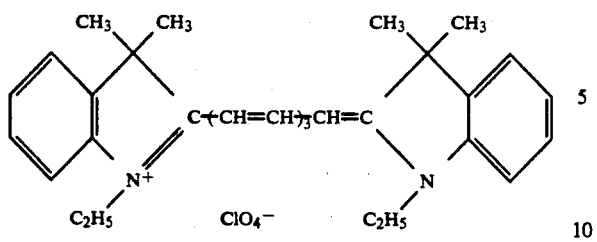

was coated on a glass plate (50×50×1 mm) substrate, forming a dye film of 0.08 μm thick.

After drying, an aqueous solution containing 1% by weight of a chemical substance sensitive compound, sodium alginate having an SP value of at least 20 $(MJ/m^3)^{\frac{1}{2}}$ and a contact angle of up to 70° was coated on the dye film, forming a coating of 0.06 μm. The coated substrate was then immersed in an aqueous solution of 2% by weight of $CaCl_2$ for one minute for salt exchange.

The substrate was taken out of the solution and dried on a spinner. It was further dried in a dryer (70° C., 1 hour). There was formed a chemical substance sensitive film containing the Ca alginate salt and $CaCl_2$.

Using the glass substrate having the chemical substance sensitive film formed via the dye film, a sensing device of the configuration shown in FIG. 2 was constructed.

The light emitting element used was an LED emitting light at a wavelength of 950 nm and the light receiving element used was a PIN diode.

On use in humidity measurement, the sensing device could measure water vapor over a concentration range of 30 to 90% RH.

Figure 10:
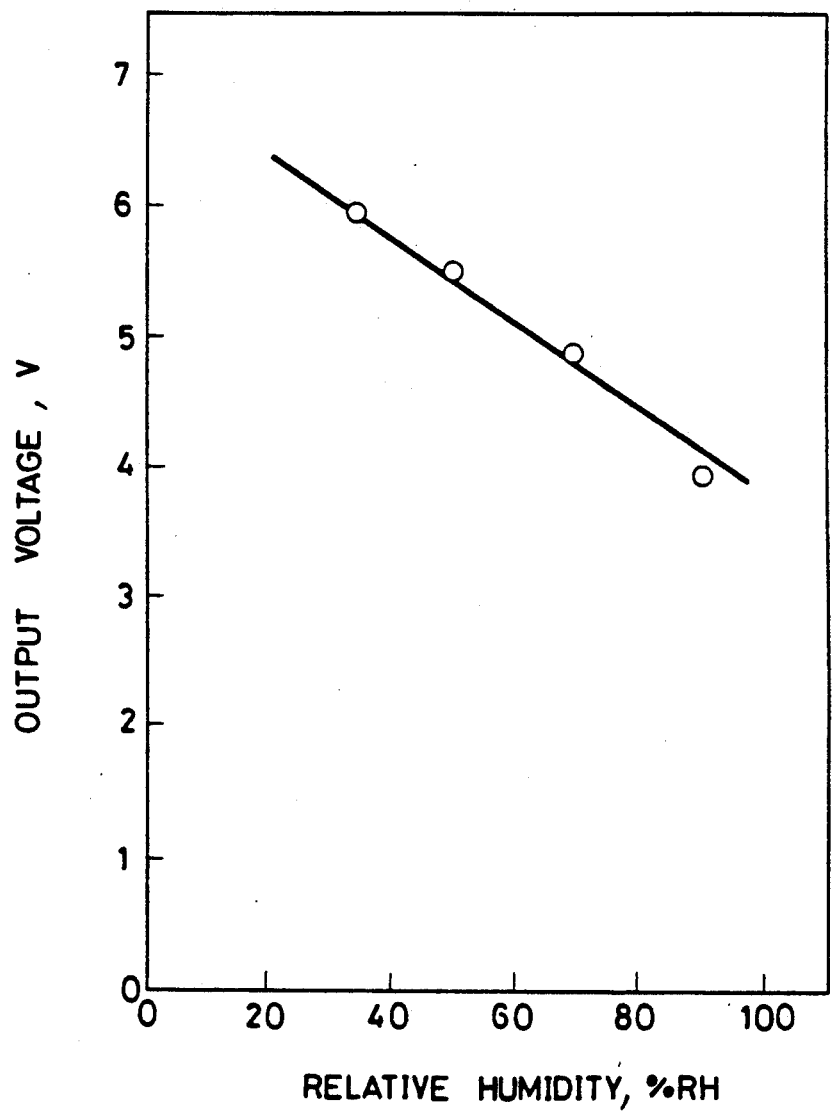

FIG. 10 shows the relationship of the output voltage of the sensing device to relative humidity.

The results show that the concentration was measurable over a wide range with improved linearity.

EXAMPLE 8

A sensor film was formed by the same procedure as in Example 7 using a transparent PET (manufactured by Teijin K. K., 0.2 mm thick) as the substrate and a naphthalocyanine dye of the following structure:

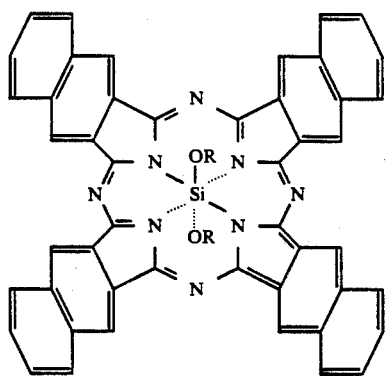

$(R = -Si(CH_3)_2-O+CH_2CH_2O)_3C_4H_9)$ as the dye. A sensing device constructed therefrom was found to produce a substantially linear output change over a range of 30 to 90% RH.

EXAMPLE 9

A sensor film was formed by the same procedure as in Example 7 using a glass plate as the substrate and a cyanine/Ni complex of the following structure:

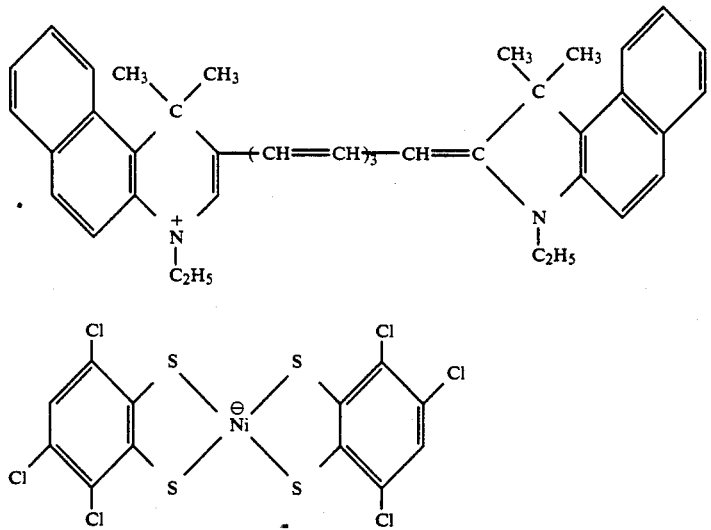

as the dye. A sensing device was similarly constructed. A substantially linear output change was observed over a range of 30 to 90% RH.

EXAMPLE 10

A sensor film was formed by the same procedure as in Example 7 using a transparent PET as the substrate, a phthalocyanine dye of the following structure:

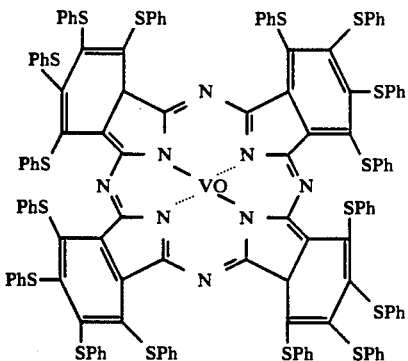

as the dye, and sodium poly(4-styrenesulfonate) having an SP value of at least 20 $(MJ/m^3)^{\frac{1}{2}}$ and a contact angle of up to 70° as the chemical substance sensitive compound. A sensing device was similarly constructed. Again, a substantially linear relationship was observed over a range of 30 to 90% RH.

EXAMPLE 11

A methanol solution containing 2% by weight of a dye:

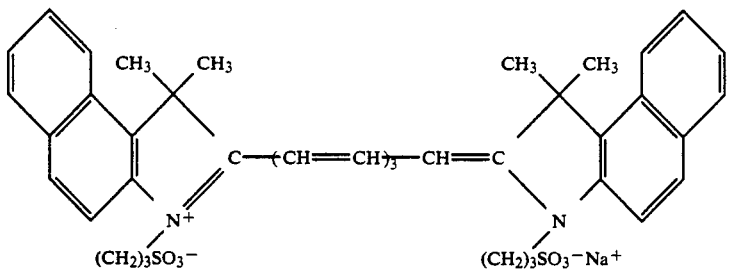

was coated on a glass substrate (50×50×1 mm), forming a dye film of 0.08 μm thick. After drying, the coated substrate was immersed in an aqueous solution of 5% by weight of $CaCl_2$ for 40 seconds for salt exchange.

After drying, a cyclohexanone solution containing 2% by weight of a humidity-sensitive, hydrophilic compound, acetylcellulose having an SP value of 23 $(MJ/m^3)^{\frac{1}{2}}$ and a contact angle of up to 70° was coated on the dye film, forming a coating of 0.1 μm.

Figure 11:
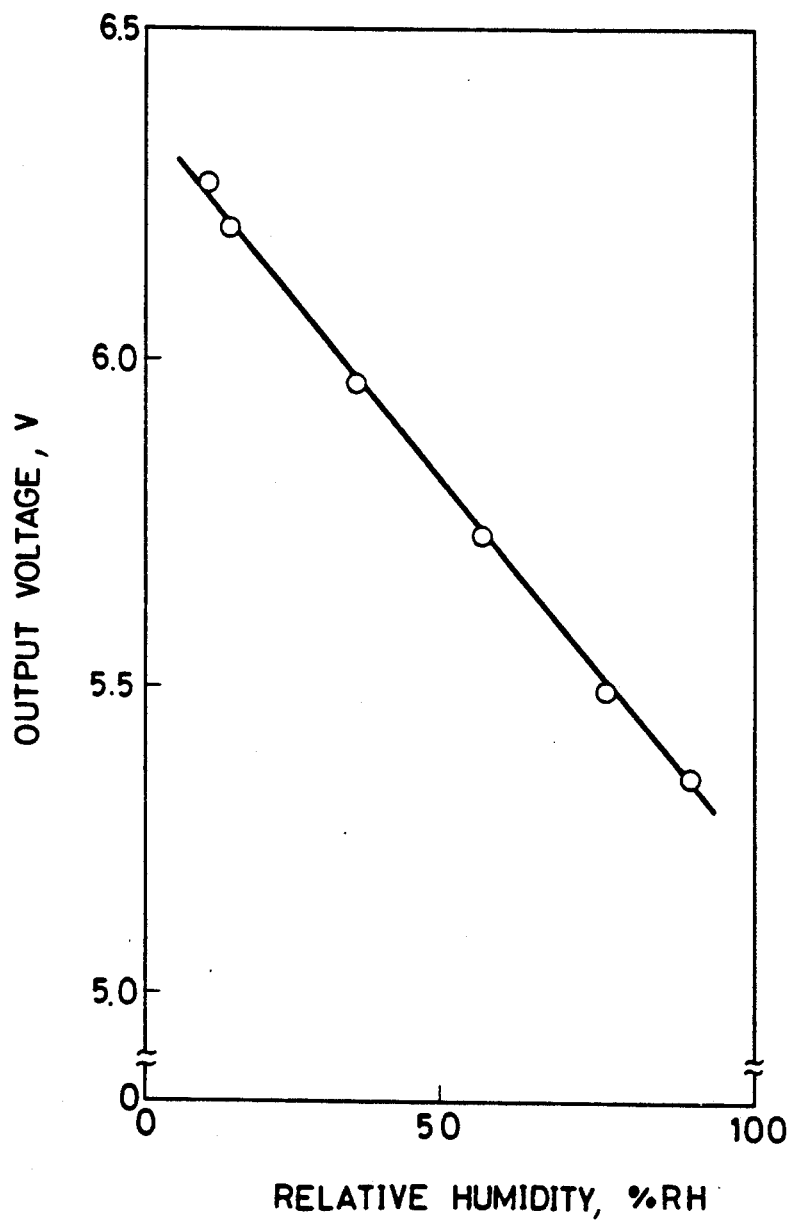

On use in humidity measurement, the thus constructed sensing device showed a substantially linear output change over a concentration range of 10 to 90% RH as seen from FIG. 11.

EXAMPLE 12

A sensing device was constructed as in Example 11 except that the humidity-sensitive compound used was ethyl cellulose having an SP value of 21 $(MJ/m^3)^{\frac{1}{2}}$ and a contact angle of up to 70°. Similarly, it showed a substantially linear output change over a concentration range of 10 to 90% RH.

EXAMPLE 13

A sensing device was constructed as in Example 11 except that the humidity-sensitive compound used was triacetylcellulose having an SP value of about 20 $(MJ/m^3)^{\frac{1}{2}}$ and a contact angle of up to 70°. Similarly, it showed a substantially linear output change over a concentration range of 10 to 90% RH.

We claim:

1. A chemical substance-sensing element in the form of a sensor film comprising a dye selected from the group consisting of cyanine dyes, azulenium dyes, pyrylium dyes, squarilium dyes, chloconium dyes, quinone-naphthoquinone dyes, metal complex dyes, phthalocyanine dyes and naphthalocyanine dyes, and a chemical substance-sensitive compound selected from the group consisting of a hydrophilic high-molecular weight compound, a hydrophilic low-molecular weight organic compound, a hydrophilic inorganic compound, Bromothymol Blue, Thymol Blue, Acridine Orange, poly-2-para-(methacryloylaminophenyl)-5-phenyl-1,3-oxazole and a crown ether, wherein said chemical substance sensitive compound changes its physical properties when the chemical substance-sensitive compound bonds with a chemical substance to be detected whereby the reflectance of said film changes without substantial color change of the dye.

2. The chemical substance-sensing element of claim 1 wherein said hydrophilic compound has a solubility parameter SP of at least 17 $(MJ/m^3)^{\frac{1}{2}}$.

3. The chemical substance-sensing element of claim 1 wherein said hydrophilic compound has a contact angle with water of up to 70° when formed as a monolayer film.

4. The chemical substance-sensing element of claim 1 wherein the chemical substance to be detected is ammonia and said chemical substance sensitive compound is at least one member selected from the group consisting of Bromothymol Blue, Thymol Blue, Acridine Orange, and poly-2-para-(methacryloylaminophenyl)-5-phenyl-1,3-oxazole.

5. The chemical substance-sensing element of claim 1 wherein the chemical substance to be detected is a metal ion and said chemical substance sensitive compound is a crown ether.

6. The chemical substance-sensing element of claim 1 wherein said hydrophilic compound is at least one member selected from the group consisting of a hydrophilic high-molecular weight compound, a hydrophilic low-molecular weight organic compound, and a hydrophilic inorganic compound.

7. The chemical substance-sensing element of claim 6 wherein said hydrophilic compound is a hydrophilic high-molecular weight compound containing a polar group.

8. The chemical substance-sensing element of claim 1 wherein the sensor film comprising a dye and a chemical substance sensitive compound is on a substrate.

9. The chemical substance-sensing element of claim 8 wherein the sensor film comprises a mixture of a dye and a chemical substance sensitive compound and when said chemical substance sensitive compound bonds with the chemical substance, said film changes its thickness or refractive index whereby the reflectance of said film changes without substantial color change of the dye.

10. The chemical substance-sensing element of claim 9 wherein the sensor film is 400 to 2,000 Å thick.

11. The chemical substance-sensing element of claim 9 wherein said chemical substance sensitive compound is present in an amount of 0.01 to 40% by weight based on the weight of said dye.

12. The chemical substance-sensing element of claim 8 wherein said sensor film is a laminate of a dye film containing a dye and a chemical substance sensitive film containing a chemical substance sensitive compound and when said chemical substance sensitive compound bonds with the chemical substance, said chemical substance sensitive film changes is thickness or refractive index whereby the reflectance of said sensor film changes without substantial color change of the dye.

13. The chemical substance-sensing element of claim 12 wherein in said laminate, said dye film is disposed adjacent the substrate with respect to said chemical substance sensitive film.

14. The chemical substance-sensing element of claim 12 wherein said chemical substance sensitive film is 0.05 to 100 μm thick and said dye film is 400 to 2,000 Å thick.

15. The chemical substance-sensing element in the form of a sensor film comprising a dye and a chemical substance-sensitive compound, wherein said sensor film has reflectance of at least 10% at the wavelength of light-emitting element; and said chemical substance sensitive compound changes its physical properties when the chemical substance-sensitive compound bonds with a chemical substance to be detected whereby the reflectance of said film changes without substantial color change of the dye, wherein said dye is selected from the group consisting of cyanine dyes, azulenium dyes, pyrylium dyes, squarilium dyes, chloconium dyes, quinone-naphthoquinone dyes, metal complex dyes, phthalocynine dyes and naphthalocyanine dyes, and said chemical substance-sensitive compound is selected from the group consisting of a hydrophilic high-molecular weight compound, a hydrophilic low-molecular weight compound, a hydrophilic inorganic compound, Bromothymol Blue, Thymol Blue, Acridine Orange, poly-2-para-(methacryloylaminophenyl)-5-phenyl-1,3-oxazole and a crown ether.

* * * * *

UNITED STATES PATENT AND TRADEMARK OFFICE
CERTIFICATE OF CORRECTION

PATENT NO. : 5,268,145
DATED : December 7, 1993
INVENTOR(S) : Kenryo Namba et al.

It is certified that error appears in the above-indentified patent and that said Letters Patent is hereby corrected as shown below:

On the title page, Item [30],

The first Foreign Application Priority number, should read:

--63-219434--

Signed and Sealed this

Seventh Day of June, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,268,145
DATED : December 7, 1993
INVENTOR(S) : Kenryo Namba et al It is certified that error appears in the above-indentified patent and that said Letters Patent is hereby corrected as shown below:

Column 21,

Claim 12, line 7, change "is" to --its--.

Signed and Sealed this

Twenty-seventh Day of September, 1994

Attest:

BRUCE LEHMAN

*Attesting Officer*  *Commissioner of Patents and Trademarks*